US006716865B1

(12) United States Patent
Billich et al.

(10) Patent No.: US 6,716,865 B1
(45) Date of Patent: Apr. 6, 2004

(54) BENZOXA- AND BENZTHIAZOLES

(75) Inventors: Andreas Billich, Moedlin (AT); Erwin Paul Schreiner, Vienna (AT); Barbara Wolff-Winiski, Vienna (AT)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 10/130,567

(22) PCT Filed: Nov. 17, 2000

(86) PCT No.: PCT/EP00/11475

§ 371 (c)(1),
(2), (4) Date: May 17, 2002

(87) PCT Pub. No.: WO01/36398

PCT Pub. Date: May 25, 2001

(30) Foreign Application Priority Data

Nov. 19, 1999 (GB) .............................................. 9927439
Mar. 28, 2000 (GB) .............................................. 0007511

(51) Int. Cl.[7] ..................... C07D 263/56; A61K 31/423
(52) U.S. Cl. ....................... 514/375; 514/367; 548/178; 548/217
(58) Field of Search ................................ 548/178, 217; 514/367, 375

(56) References Cited

U.S. PATENT DOCUMENTS

| | | | |
|---|---|---|---|
| 2,868,800 A | 1/1959 | Korman | |
| 4,472,418 A | 9/1984 | Woltersdorf | |
| 5,192,785 A | 3/1993 | Lo et al. | |
| 5,194,446 A | 3/1993 | Lo et al. | |
| 5,273,993 A | 12/1993 | Lo et al. | |
| 5,709,845 A | 1/1998 | Rajagopalan et al. | |
| 6,011,045 A | 1/2000 | Wehner et al. | |
| 6,380,188 B1 * | 4/2002 | Getman et al. | 514/228.2 |

FOREIGN PATENT DOCUMENTS

| | | |
|---|---|---|
| EP | 0 283 035 | 9/1988 |
| JP | 10-237053 | 9/1999 |
| WO | WO 92/20642 | 11/1992 |
| WO | WO 93/11120 | 6/1993 |
| WO | WO 94/08962 | 4/1994 |
| WO | WO 96/11917 | 4/1996 |
| WO | WO 97/31636 | 9/1997 |
| WO | WO 99/03849 | 1/1999 |
| WO | WO 99 27935 | 6/1999 |
| WO | WO 99/52890 | 10/1999 |
| WO | WO 99/65886 | 12/1999 |

OTHER PUBLICATIONS

Corral et al; Anales de Fisica Y Quimica, "Activdad Anticolesterasica de una Serie de N,N–Dimetilsulfamatos de Arilo," pp. 341–344 (1964) (see attached English abstract).

Fiorentino et al; J. Chem. Soc., vol. 2, "Displacement of the Acyl Group in Benzothiazoles by Nucleophilic Alkyl Radicals. Homolytic Aromatic ipsol–Sustitution", pp. 1679–1683 (1977).

Li et al; J. Steroid Biochem. Molec. Biol., vol. 59(1), "Synthesis and Sulfatase Inhibitory Activities of Non–steroidal Estrone Sulfatase Inhibitors", pp. 41–48 (1996).

Purohit et al; Cancer Research, vol. 56, In Vivo Activity of 4–Methycoumarin–7–O–Sulfamate, a Nonsteroidal, Non-estrogenic Steroid Sulfatase Inhibitor[1], pp. 4950–4955 (1996).

Sanfilippo et al; J. Med. Chem. vol. 31, Synthesis of (Aryloxy)alkylamines. 1. Novel Antisecretory Agents with $H^+K^+$–ATPase Inhibitory Activity, pp. 1778–1785 (1988).

Woltersdorf, Jr.. et al; J. Med. Chem. vol. 32, No. 11, "Topically Active Carbonic Anhydrase Inhibitors.", pp. 2486–2492 (1989).

Woo et al; J. Med. Chem., vol. 39, "Active Site Directed Inhibition of Estrone Sulfatase by Nonsteroidal Coumarin Sulfamates", pp. 1349–1351 (1996).

Costantini et al, Tetrahedron Letters, vol. 35, No., "Photochemical Ring Contraction of Dihydro–1,4–benzothiazines", pp. 3365–3366 (1994).

Derwent Abstracts 96–518600/51 (WO 96/35688–A1—Nov. 14, 1996).

Chemical Abstracts No. 14075u, vol. 75, p. 316 (1971).

Derwent Abstracts 98–537451/46 (JP 10237053–A—Sep. 8, 1998.

"Steroidal and Nonsteroidal Sulfamates as Potent Inhibitors of Steroid Sulfatase", Journal of Medicinal Chemistry, Vol 41 No. 7, pp. 1068–1083, Mar. 26, 1998.

* cited by examiner

*Primary Examiner*—Robert Gerstl
(74) *Attorney, Agent, or Firm*—D. Gabrielle Brouillette; Carol Loeschorn

(57) ABSTRACT

Benzoxa- and benzthiazoles substituted at the 2 position and carrying a sulfamic acid ester group bound via oxygen to the phenyl part of the ring structure, such as the compounds of formula (I) wherein the symbols have various significances, possess interesting pharmacological activity. They can be prepared by sulfamoylation of a corresponding compound carrying a hydroxy group on the phenyl part of the ring structure, or by N-substitution. They are indicated for use as steroid sulfatase inhibitors in the prevention and treatment of illnesses responsive to steroid sulfatase inhibition, such as acne.

9 Claims, No Drawings

BENZOXA- AND BENZTHIAZOLES

The invention relates to benzoxa- and benzthiazole derivatives. It concerns a benzoxa- or benzthiazole substituted at the 2 position and carrying a sulfamic acid ester group bound via oxygen to the phenyl part of the ring structure, hereinafter briefly named "a compound of the invention".

More specifically, it concerns a compound of formula I $$\underset{R_2}{\overset{R_1}{N}}-\underset{\underset{O}{\overset{O}{\|}}}{\overset{\|}{S}}-O-\underset{6}{\overset{5}{\text{benzazole}}}-R_3 \quad \text{I}$$

wherein
- X is O or S;
- $R_1$ and $R_2$ either independently are hydrogen or alkyl, or one is hydrogen and the other is acyl or alkoxycarbonyl; and
- $R_3$ is alkyl; alkenyl; alkinyl; cycloalkyl; cycloalkenyl; aryl; acyl; cycloalkylalkyl; cycloalkylalkenyl, including cycloalkanylidenealkyl; cycloalkenylalkyl; arylalkyl; arylalkenyl; arylalkinyl; alkoxycarbonylaminoalkyl; hydroxycycloalkylalkyl; cycloalkanylidenecycloalkanylidenalkyl; heteroaryl; or heteroarylalkyl;

in free form or salt form.

The sulfamoyloxy moiety in formula I is bound to the ring system in position 5 or 6, preferably 6.

Alkyl as a group $R_1$ or $R_2$ preferably is of 1 to 4 carbon atoms, it especially is methyl. Acyl as a group $R_1$ or $R_2$ preferably is formyl or alkylcarbonyl of altogether 2 to 5 carbon atoms, it especially is acetyl. Alkoxycarbonyl as a group $R_1$ or $R_2$ preferably is of altogether 2 to 5 carbon atoms, it especially is methoxycarbonyl.

In significance $R_3$:
- akyl as such or as part of a substituent such as cycloalkylalkyl includes $(C_{1-22})$alkyl, e.g. $(C_{1-16})$alkyl and $(C_{1-4})$alkyl;
- alkenyl as such or as part of a substituent such as cycloalkylalkenyl includes $(C_{2-22})$alkenyl, e.g. $(C_{2-16})$alkenyl and $(C_{2-4})$alkenyl; when it is part of cycloalkanylidenealkyl the double bond is attached directly to the cycloalkyl moiety and thus the alkenyl part of such a cycloalkylalkenyl group is to be viewed as consisting of just one carbon atom;
- alkinyl as such or as part of a substituent such as arylalkinyl includes $(C_{2-22})$alkinyl;
- cycloalkyl as such or as part of a substituent such as cycloalkylalkyl or hydroxycycloalkylalkyl includes $(C_{4-12})$cycloalkyl, such as cyclobutyl, cyclopentyl, cyclohexyl, cycloheptyl, and cyclododecanyl; it may be mono- or polycyclic, such as bridged cycloalkyl, as in adamantyl, hexahydro-2,5-methanopentalenyl; bicyclo[3.3.1]nonyl, or it may be cycloalkyl annexed to a second ring system, e.g. a second cycloalkyl, such as decalin (octahydronaphthyl), and includes spiro cycloalkyl, as in 1,4-dioxo-spiro[4.5]decyl or 1,5-dioxo-spiro[5.5] undecyl, whereby the cycloalkyl moiety and the annexed second ring system are unsubstituted or substituted with e.g up to 4, preferably one or two alkyl or alkoxy moieties of preferably 1 or 2 carbon atoms; when cycloalkyl is part of a substituent, there preferably is just one, but there may be up to two, mono- or polycyclic cycloalkyl moieties, as in e.g. dicyclohexylmethyl;
- cycloalkenyl as such or as part of cycloalkenylalkyl includes $(C_{4-12})$cycloalkenyl, such as cyclohexenyl; it may be polycyclic, as in e.g. decahydrophenanthrenyl, and may be substituted, e.g. with 1 to 3 $(C_{1-4})$alkyl;
- aryl as such or as part of arylalkyl, arylalkenyl or arylalkinyl includes $(C_{5-18})$aryl, e.g. $(C_{5-12})$aryl, e.g. phenyl or tetrahydronaphthalinyl, and may be substituted by e.g. alkyl; there may be up to 3, preferably 1 aryl moiety when aryl is part of a substituent, as in di- or triphenylmethyl;
- aryl includes the residue of a carboxylic acid, in particular an alkyl, aralkyl or aryl carboxylic acid, e.g. an alkyl, aralkyl or aryl carbocyclic acid;
- cycloalkylalkenyl includes e.g. a cycloalkanylidenalkyl group of formula i $$\underset{R_8}{\overset{R_4 \quad R_5}{\diagup\!\!\!\!=\!\!\!\!\diagdown}} \quad \text{i}$$

wherein
- $R_4$ is hydrogen or alkyl, e.g. $(C_{1-4})$alkenyl, especially methyl, and
- $R_5$ and $R_6$ together with the carbon atom to which they are attached form cycloalkyl;
- cycloalkenylalkyl is e.g. cyclohexenylmethyl;
- alkoxycarbonylaminoalkyl is e.g. tert-butoxycarbonylamino-2,2-dimethylpropyl;
- in hydroxycycloalkylalkyl the hydroxy group preferably is bound to the cycloalkyl part at the same carbon atom that is bound to the alkylene part of the hydroxycycloalkylalkyl moiety;
- cycloalkanylidenecycloalkanylidenalkyl is e.g. bicyclobutylidenylidenemethyl;
- heteroaryl as such or as part of heteroarylalkyl preferably is pyridyl or thienyl.

X preferably is oxygen, $R_1$ and $R_2$ preferably are hydrogen. $R_3$ preferably is alkyl; cycloalkylalkyl; cycloalkenylalkyl; alkoxycarbonylaminoalkyl; or cycloalkylalkenyl, e.g. a group of formula i as defined above.

A subgroup of compounds of the invention is the compounds of formula I wherein
- X is as defined above;
- $R_1$ and $R_2$ are hydrogen; and
- $R_3$ is alkyl, alkenyl, cycloalkyl or cycloalkenyl, in free form or salt form.

A further subgroup of compounds of the invention is the compounds of formula Is $$H_2N-\underset{\underset{O}{\overset{O}{\|}}}{\overset{\|}{S}}-O-\underset{6}{\overset{5}{\text{benzazole}}}-\overset{R_4}{\underset{R_6}{\diagup\!\!\!\!=\!\!\!\!\diagdown}}R_5 \quad \text{Is}$$

wherein X, $R_4$, $R_5$ and $R_6$ are as defined above; in free form or salt form.

A further subgroup of compounds of the invention is the compounds of formula It

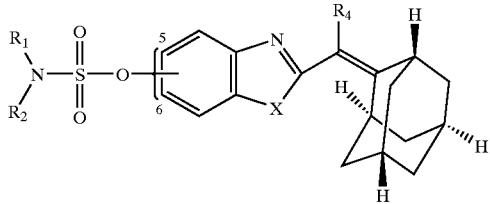

wherein X, $R_1$, $R_2$ and $R_4$ are as defined above; in free form or salt form; e.g. sulfamic acid 2-(adamantan-2-ylidenemethyl)benzoxazol-6-yl ester in free form or salt form.

A further subgroup of compounds of the invention is the compounds of formula $I_{p1}$

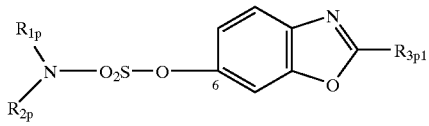

wherein
either $R_{1p}$ and $R_{2p}$ have the significances indicated above for $R_1$ and $R_2$; and
$R_{3p1}$ is alkyl; alkenyl; alkinyl; cycloalkyl; acyl; cycloalkylalkyl; arylalkyl; arylalkenyl; arylalkinyl; heteroaryl; or heteroarylalkyl;
or $R_{1p}$ and $R_{2p}$ are hydrogen; and
$R_{3p1}$ is adamantan-2-ylidenemethyl;
in free form or salt form.

A further subgroup is the compounds of formula $I_{p2}$

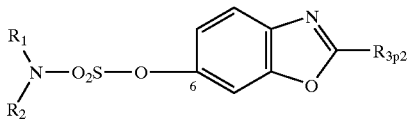

wherein
$R_1$ and $R_2$ are as defined above; and
$R_{3p2}$ is alkyl; alkenyl; alkinyl; cycloalkyl; acyl; cycloalkylalkyl; adamantylalkenyl, including adamantanylidenalkyl; arylalkyl; arylalkenyl; arylalkinyl; heteroaryl; or heteroarylalkyl;
in free form or salt form.

A further subgroup is the compounds of formula Iq

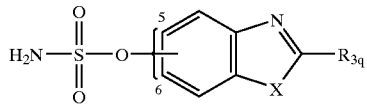

wherein X is as defined above and
$R_{3q}$ is
$(C_{1-13})$alkyl;
$(C_{10-16})$alkenyl;
cycloalkyl selected from adamantyl and hexahydro-2-5-methano-pentalenyl;
the cycloalkenyl moiety 7-isopropyl-1,4a-dimethyl-1,2,3,4,4a,4b,5,6,10,10a-decahydrophenanthren-1-yl;
an aryl moiety 5,6,7,8-tetrahydronaphthalenyl;
cycloalkyl selected from adamantylalkyl of 1 to 4 carbon atoms in the alkylene part thereof and dicyclohexylmethyl;
cycloalkylalkenyl (including cycloalkanylidenalkyl) selected from:
adamantanyliden$(C_{1-4})$alkyl; $(C_{4-12})$cycloalkylidene $(C_{1-4})$alkyl; bicyclo[3.3.1]nonylidenemethyl; dimethylcyclohexylidenemethyl; $(C_{1-4})$alkoxycyclohexylidenemethyl; $(C_{1-4})$alkylcyclohexylidenemethyl; tetra$(C_{1-4})$alkylcyclohexylidenemethyl; 1,4-dioxaspiro[4.5]dec-8-ylidenemethyl; 3,3-dimethyl-1,5-dioxo-spiro[5.5]undec-9-ylidenemethyl; and octahydronaphthalylidenemethyl;
cyclohexenyl$(C_{1-4})$alkyl;
arylalkyl selected from di- or triphenyl$(C_{1-4})$alkyl;
$(C_{1-4})$alkoxycarbonylamino$(C_{1-6})$alkyl;
hydroxycycloalkylalkyl selected from:
(2-hydroxyadamant-2-yl)$(C_{1-6})$alkyl;
(9-hydroxybicyclo[3.3.1]non-9-yl$(C_{1-4})$alkyl; and
1-hydroxy-2,2-dimethylcyclohexyl$(C_{1-4})$alkyl; or
a cycloalkanylidenecycloalkanylidenalkyl moiety bicyclobutylidenylidenemethyl;
in free form or salt form.

A compound of the invention includes a compound in any form, e.g. in free form, in the form of a salt, in the form of a solvate and in the form of a solvated salt.

A salt of a compound of the invention includes a pharmaceutically acceptable salt, e.g. an acid addition salt. A compound of the invention in free form may be converted into a corresponding compound in the form of a salt and vice versa. A compound of the invention in the form of a solvate in free form or salt form may be converted into a corresponding compound in free form or salt form in unsolvated form and vice versa.

A compound of the invention may exist in the form of isomers and mixtures thereof; e.g. a compound of the invention may contain substituents exhibiting geometric isomerism and/or asymmetrically substituted carbon atoms and may thus exist in the form of isomers and/or diastereoisomers and mixtures thereof. Isomeric mixtures may be separated in conventional manner to obtain pure isomers or diastereoismers, respectively, The invention includes a compound of the present invention in any isomeric and/or diastereoisomeric pure form and in the form of any isomeric and/or diastereoisomeric mixture.

The invention further includes a process for the preparation of a compound of the invention as defined above, comprising sulfamoylating a corresponding benzoxa- or benzthiazole substituted in the 2 position and carrying a hydroxy group on the phenyl part of the ring structure.

More specifically, it concerns a process for the preparation of a compound of formula I as defined above, in free form or salt form, comprising
a) when $R_1$ and $R_2$ are both hydrogen, sulfamoylating a compound a formula II

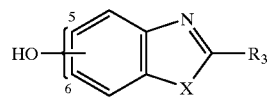

wherein X and $R_3$ are as defined above, or
b) when one or of both $R_1$ and $R_2$ are other than hydrogen, appropriately N-substituting a compound of formula I wherein $R_1$ and $R_2$ are both hydrogen, and recovering the resultant compound of formula I in free form or salt form.

The process of the invention may be effected in conventional manner.

Process variant a) may be carried out e.g. by reacting a compound of formula II a1) with sulfuryl chloride and sodium- or potassium azide, and reducing the azide group to an amino group —NH$_2$ in a resultant compound of formula III

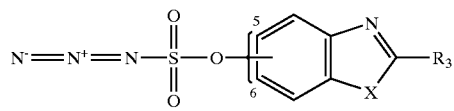

III wherein X and R$_3$ are as defined above; or a2) with Cl—SO$_2$—NCO and submitting the product obtained to aqueous hydrolysis; or a3) with a compound of formula IV

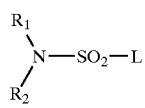

IV wherein R$_1$ and R$_2$ are both hydrogen and L is a leaving group, e.g. halogen, preferably chloro; such as H$_2$N—SO$_2$—Cl;

e.g. in an inert solvent, e.g. dimethylformamide or dimethylacetamide, with or without addition of an organic base, such as an organic tertiary amine, or an inorganic base, e.g. an alkali(hydrogen)carbonate or alkali hydride, preferably sodium hydride.

Process variant b) may be effected by N-alkylating, N-acylating or N-alkoxycarbonylating using e.g. for N-alkylation activated alkyl, e.g. alkyl halogenides, such as alkyl iodides, alkyl sulfates or alkyl mesy(tosy)lates; for N-acylation acyl halogenides; and for N-alkoxycarbonylation alkoxycarbonyl halides, preferably chlorides. The reaction is effected conveniently in the presence of a suitable base, preferably an alkali metal carbonate or alkali metal hydride, preferably in an inert, preferably polar solvent such as acetone or dimethylformamide, at temperatures between about −20° and about +120° C., preferably between room temperature and about 60° C.

A resultant compound of the invention may be recovered from the reaction mixture and isolated and purified in conventional manner. Isomers, such as geometric isomers or enantiomers or diastereoisomers, may be obtained in conventional manner, e.g. by fractional crystallization or asymmetric synthesis from corresponding asymmetrically substituted, e.g. optically active starting materials.

The starting materials may also be prepared in conventional manner. A compound of formula II may e.g. be obtained by α) reacting a compound of formula V

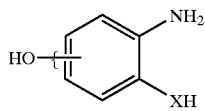

V wherein X is as defined above, with a compound of formula R$_3$—COHal, wherein Hal is halogen, e.g. chloro, and R$_3$ is as defined above and, if desired, further reacting a resultant compound of formula II with sulfuryl chloride and sodium- or potassium azide to obtain a compound of formula III; or β) for the production of a compound of formula IIa

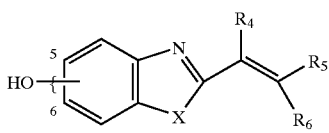

IIa wherein X, R$_4$, R$_5$ and R$_6$ are as defined above, reacting a compound of formula IIb

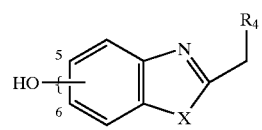

IIb wherein R$_4$ and X are as defined above, with a compound of formula VI

VI wherein R$_5$ and R$_6$ are as defined above, e.g. in the presence of trimethylsilyl chloride (TMSCl), N-ethyldiisopropylamine and sodium bis(trimethylsilyl)amide in an inert solvent, e.g. tetrahydrofurane, at low temperatures, e.g. around −70° C., and dehydrating a resultant compound of formula IIc

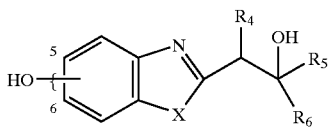

IIc wherein X, R$_4$, R$_5$ and R$_6$ are as defined above, e.g. by treatment with trifluoroacetic acid in an inert solvent such as toluene.

Process variant a3) above is also indicated for the preparation of a compound of formula I wherein R$_1$ and R$_2$ are hydrogen, X is as defined above and R$_3$ is a group of formula i as defined above, starting from a corresponding compound of formula IIc and dehydrating a resultant compound of formula I wherein R$_3$ is hydroxycycloalkylalkyl as described under β) above.

Alternatively a compound of formula II may be obtained by reaction of a compound of formula V with a compound of formula R$_3$COOH, conveniently in the presence of propylphosphonic acid anhydride and N-ethyldiisopropylamine; or 2,2'-dithiopyridine and triphenylphosphane; preferably in an inert solvent, e.g. methylene chloride, and cyclizing a resultant compound of formula VII

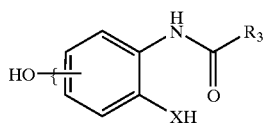

wherein X and $R_3$ are as defined above, e.g. in the presence of diethylazodicarboxylate and triphenylphosphine in an inert solvent, e.g. tetrahydrofurane, at e.g. room temperature.

Alternatively a compound of formula IIa may be obtained by reaction of a compound of formula VIII

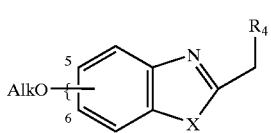

wherein X and $R_4$ are as defined above and Alk is alkyl, preferably methyl, with a compound of formula VI, e.g. in the presence of butyl lithium in an inert solvent, e.g. tetrahydrofurane, conveniently at low temperatures, such as around −70° C.,
to obtain a compound of formula IX

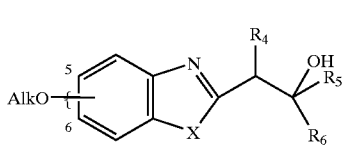

wherein Alk, X, $R_4$, $R_5$ and $R_6$ are as defined above; and either
- dealkylating to obtain a compound of formula IIc and then dehydrating, e.g. as described under β) above, to obtain a corresponding compound of formula IIa; or
- dehydrating first, e.g. as described under β) above, to obtain a compound of formula X

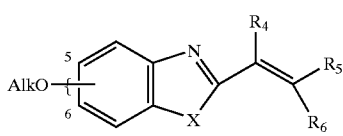

wherein Alk, X, $R_4$, $R_5$ and $R_6$ are as defined above; and then dealkyltaing to obtain a corresponding compound of formula IIa, e.g. in the presence of pyridine and HCl, conveniently at high temperatures, such as above about 100° C., e.g. around 200° C.

Many starting materials and intermediates are either known or can be prepared according to known methods or analogously as described in the Examples.

The compounds of formula IIa, IIc, IX and X in free form or salt form are novel and also form part of the invention.

The following Examples illustrate the invention. Temperatures are in degrees Celsius. NMR values are for $^{13}$C-NMR spectra at 62.9 MHz in $CDCl_3$ unless indicated otherwise. The following abbreviations are used:
DMA=dimethylamide
DMSO=dimethylsulfoxide
Ex.=Example
m.p.=melting point

EXAMPLE 1

Sulfamic Acid 2-(adamantan-1-ylmethyl) benzoxazol-6-yl Ester

[X=O; $R_1$=$R_2$=H; $R_3$=adamantan-1-ylmethyl; sulfamoyloxy moiety in position 6] [process variant a)]

74 mg 2,6-di-tert-butyl-4-methylpyridine and 83 mg amidosulfonyl chloride are added to a solution of 50 mg 2-(adamantan-1-ylmethyl)benzoxazol-6-ol (formula II) in 5 ml of a mixture of dichloromethane and dimethylformamide and the mixture obtained is stirred at room temperature for about 2 hours. The solvent is evaporated off and the residue obtained is purified by chromatography on silica gel (cyclohexane/ethyl acetate 2/1). The title compound is obtained (crystals; m.p. 147–150°); $^{13}$C-NMR: 166.556, 150.344, 147.020, 139.886, 119.423, 118.873, 105.526, 42.997, 42.300, 36.477, 33.977, 28.441.

EXAMPLES 1a AND 1b

Sulfamic Acid 2-[1-(2-hydroxyadamantan-2-yl) pentyl]benzoxazol-6-yl Ester and, Respectively, Sulfamic Acid 2-[1-(adamantan-2-ylidene)pentyl] benzoxazol-6-yl Ester

[X=O; $R_1$=$R_2$=H; $R_3$=1-(2-hydroxyadamantan-2-yl) pentyl and, respectively, 1-(adamantan-2-ylidene) pentyl; sulfamoyloxy moiety in position 6] [process variant a)]

To a solution of 100 mg 2-[1-(2-hydroxyadamantan-2-yl) pentyl]benzoxazol-6-ol (formula II) in 2 ml of dry DMA is added 100 mg sulfamoyl chloride and the reaction mixture is stirred at about 60° for about 30 minutes. To the resultant mixture are added 6 ml of an aqueous sodium acetate solution (13.1 g in 60 ml) and 10 ml of ethyl acetate at room temperature and the mixture is stirred for a few minutes. The two phases formed are separated, the organic phase is washed with sodium acetate solution and brine and dried. From the dried solution the solvent is evaporated off and the residue obtained is purified by chromatography (silica gel; ethylacetate/cyclohexane 1/2). The title compound of Example 1a, and the title compound of Example 1b, are obtained as oil; $^{13}$C-NMR;

Example 1a; 170.909, 149.692, 146.899, 139.651, 119.899, 118.934, 105.730, 76.199, 44.068, 38.109, 37.509, 34.199, 33.774, 33.588, 32.876, 27.069, 26.965, 22.584, 13.848;

Example 1b: (125.8 Mhz, $d_6$-DMSO) 166.091, 158.038, 149.590, 147.630, 119.957, 119.610, 116.214, 105.746, 39.393, 36.636, 35.022, 34.091, 31.971, 29.783, 27.643, 26.799, 22.203.

The following compounds of formula I are obtained in analogous manner using appropriate starting materials of formula II:

| Ex. No. | X | R₁ | R₂ | R₃ | Sulfamoyloxy moiety at position | m.p. |
|---|---|---|---|---|---|---|
| 2 | O | H | H | 2,2-dimethylpropyl | 6 | 140–143° |
| 3 | O | H | H | adamantan-1-yl | 6 | 97–100° |
| 4 | O | H | H | tridecyl | 6 | 99–101° |
| 5 | O | H | H | —CH₂CH(C₆H₅)₂ 2,2-diphenylethyl | 6 | 145–148° |
| 6 | O | H | H | —CH₂C(C₆H₅)₃ 2,2,2-triphenylethyl | 6 | 160–180° |
| 7 | O | H | H | —CH(C₆H₁₁)₂ dicyclohexylmethyl | 6 | 66–72° |
| 8 | O | H | H | 1-tert-butoxycarbonylamino-2,2-dimethylpropyl | 6 | oil; NMR* |
| 9 | O | H | H | hexahydro-2,5-methanopentalen-3a-yl | 6 | 164–166° |
| 10 | O | H | H | 7-isopropyl-1,4a-dimethyl-1,2,3,4,4a,4b,5,6,10,10a-decahydrophenanthren-1-yl | 6 | 92–99° |
| 11 | O | H | H | tert-butyl | 6 | 172–174° |

-continued

| Ex. No. | X | $R_1$ | $R_2$ | $R_3$ | Sulfamoyloxy moiety at position | m.p. |
|---|---|---|---|---|---|---|
| 12 | O | H | H | adamantan-2-ylidenemethyl | 6 | 170–172°; NMR* |
| 13 | O | H | H | cyclohexylidenemethyl | 6 | 149–152° |
| 14 | O | H | H | cyclobutylidenemethyl | 6 | 129–131° |
| 15 | O | H | H | cyclopentylidenemethyl | 6 | 110–117° |
| 16 | O | H | H | cycloheptylidenemethyl | 6 | 159–161° |
| 17 | O | H | H | cyclododecanylidenemethyl | 6 | 161–174° |
| 18 | O | H | H | bicyclo[3.3.1]non-9-ylidenemethyl | 6 | 161–163° |
| 19 | O | H | H | 9-hydroxy-bicyclo[3.3.1]non-9-ylmethyl | 6 | oil |
| 20 | O | H | H | 2,2-dimethyl-cyclohex-(E)-ylidenemethyl | 6 | oil |

-continued

| Ex. No. | X | R₁ | R₂ | R₃ | Sulfamoyloxy moiety at position | m.p. |
|---|---|---|---|---|---|---|
| 21 | O | H | H | 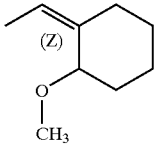<br>2-methoxy-cyclohex-(Z)-ylidenemethyl | 6 | 115–117° |
| 22 | O | H | H | 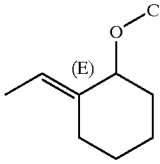<br>2-methoxy-cyclohex-(E)-ylidenemethyl | 6 | 156–159° |
| 23 | O | H | H | 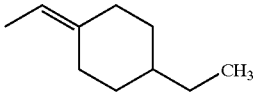<br>4-ethyl-cyclohexylidenemethyl | 6 | 151–153° |
| 24 | O | H | H | 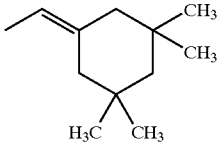<br>3,3,5,5-tetramethyl-cyclohexylidenemethyl | 6 | 130–135° |
| 25 | O | H | H | 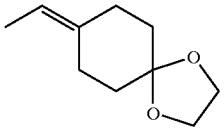<br>1,4-dioxa-spiro[4.5]dec-8-ylidenemethyl | 6 | 195–199° |
| 26 | O | H | H | 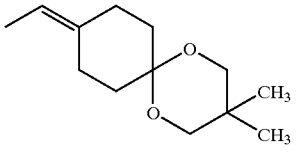<br>3,3-dimethyl-1,5-dioxa-spiro[5.5]undec-9-ylidenemethyl | 6 | 169–172° |
| 27 | O | H | H | 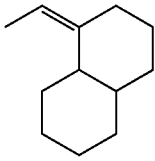<br>octahydro-naphthal-1-ylidenemethyl | 6 | 194–195° |
| 28 | O | H | H | 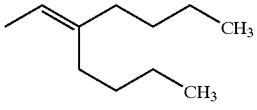<br>2-butylhex-1-ylidene | 6 | oil; NMR* |

-continued

| Ex. No. | X | R₁ | R₂ | R₃ | Sulfamoyloxy moiety at position | m.p. |
|---|---|---|---|---|---|---|
| 29 | O | H | H | 2-pentylhept-1-ylidene | 6 | oil; NMR* |
| 30 | O | H | H | 2-hexyloct-1-ylidene | 6 | oil; NMR* |
| 31 | O | H | H | 2-heptylnon-1-ylidene | 6 | oil; NMR* |
| 32 | O | H | H | 1-(2-hydroxy-adamantan-2-yl)ethyl | 6 | oil |
| 33 | O | H | H | 1-(adamantan-2-ylidene)ethyl | 6 | 178–180° |
| 34 | O | H | H | 2-hydroxyadamantan-2-ylmethyl | 6 | oil |
| 35 | S | H | H | cycloheptylidenemethyl | 5 | oil; NMR* |
| 36 | O | H | H | 5,6,7,8-tetrahydronaphthalen-1-yl | 6 | 161–163° |

-continued
| Ex. No. | X | R₁ | R₂ | R₃ | Sulfamoyloxy moiety at position | m.p. |
|---|---|---|---|---|---|---|
| 37 | O | H | H | 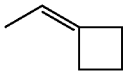 cyclobutylidenemethyl | 5 | 180–185° |
| 38 | O | H | H | 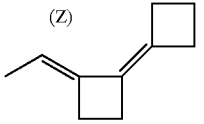 bicyclobutylidene-(2Z)-ylidenemethyl | 5 | 200° |
| 39 | O | H | H | 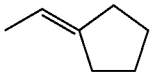 cyclopentylidenemethyl | 5 | 166–169° |
| 40 | O | H | H | 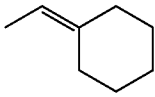 cyclohexylidenemethyl | 5 | 173–176° |
| 41 | O | H | H | 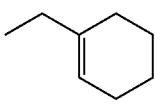 cyclohex-1-enylmethyl | 5 | 174–176° |
| 42 | O | H | H | 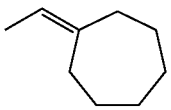 cycloheptylidenemethyl | 5 | 156–159° |
| 43 | O | H | H | 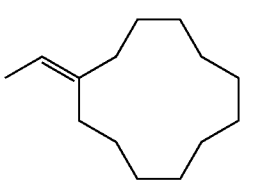 cyclododecanylidenemethyl | 5 | 148–152° |
| 44 | O | H | H |  bicyclo[3.3.1]non-9-ylidenemethyl | 5 | 175–178° |
| 45 | O | H | H | 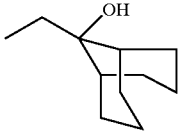 9-hydroxy-bicyclo[3.3.1]non-9-ylmethyl | 5 | oil |

-continued

| Ex. No. | X | R₁ | R₂ | R₃ | Sulfamoyloxy moiety at position | m.p. |
|---|---|---|---|---|---|---|
| 46 | O | H | H | 1-hydroxy-2,2-dimethylcyclohexylmethyl | 5 | oil |
| 47 | O | H | H | 2,2-dimethylcyclohexylidenemethyl | 5 | 163–166° |
| 48 | O | H | H | 2-methoxycyclohex-(Z)-ylidenemethyl | 5 | 147–150° |
| 49 | O | H | H | 2-methoxycyclohex-(E)-ylidenemethyl | 5 | 146–148° |
| 50 | O | H | H | 4-ethylcyclohexylidenemethyl | 5 | 161–164° |
| 51 | O | H | H | 3,3,5,5-tetramethyl-cyclohexylidenemethyl | 5 | 178–181° |
| 52 | O | H | H | 1,4-dioxa-spiro[4.5]dec-8-ylidenemethyl | 5 | 168–170° |
| 53 | O | H | H | 3,3-dimethyl-1,5-dioxa-spiro[5.5]undec-9-ylidenemethyl | 5 | 145–150° |

-continued

| Ex. No. | X | R₁ | R₂ | R₃ | Sulfamoyloxy moiety at position | m.p. |
|---|---|---|---|---|---|---|
| 54 | O | H | H | adamantan-2-ylidenemethyl | 5 | 138–139° |
| 55 | O | H | H | 1-(2-hydroxyadamantan-2-yl)ethyl | 5 | oil |
| 56 | O | H | H | 1-(adamantan-2-ylidene)ethyl | 5 | 188–190° |
| 57 | S | H | H | adamantan-2-ylidenemethyl | 6 | oil; NMR* |
| 58 | S | H | H | adamantan-2-ylidenemethyl | 5 | 200–205° |

*$^{13}$C-NMR:

Example 8: 166.745, 155.558, 150.600, 149.648, 147.269, 120.358, 119.394, 105.693, 64.292, 57.866, 35.634, 28.333, 26.318, 14.102.

Example 12: 168.446, 146.658, 140.656, 119.420, 118.622, 105.099, 103.659, 41.770, 40.197, 39.233, 36.789, 33.951, 27.851.

Example 28: (126.8 MHz) 164.389, 160.842, 149.534, 146.796, 140.860, 119.638, 118.531, 110.406, 105.023, 38.294, 32.437, 30.581, 30.030, 22.869, 22.406, 13.866, 13.835.

Example 29: (125.8 MHz) 160.874, 146.784, 140.909, 119.643, 118.522, 110.396, 105.037, 38.574, 32.674, 31.955, 31.506, 28.017, 27.538, 22.460, 22.277, 13.919.

Example 30: (125.8 MHz) 160.924, 146.798, 140.770, 119.592, 118.590, 110.348, 105.036, 38.639, 32.736, 31.575, 29.427, 29.003, 28.333, 27.849, 22.529, 22.496, 14.006, 13.976.

Example 31: (125.8 MHz) 160.870, 146.764, 140.969, 119.653, 118.499, 110.392, 105.021, 38.609, 32.702, 31.736, 29.733, 29.298, 29.050, 28.378, 27.886, 22.614, 14.008, Example 35: (125.8 MHz, d₆-DMSO) 167.336, 157.635, 154.176, 149.395, 132.640, 130.962, 123.041, 120.036, 118.927, 115.893.

Example 57: (d₆-DMSO) 165.887, 162.639, 151.553, 147.166, 134.719, 122.842, 121.308, 115.533, 110.953, 40.749, 38.615, 36.358, 33.594, 27.502.

Starting materials and intermediates may be obtained as follows:

A 2-(Adamantan-1-ylmethyl)benzoxazol-6-ol (formula II)

To a mixture of 424 mg 2-(adamantan-1-yl)-N-(2,4-dihydroxyphenyl)acetamide (formula VII) and 1.18 g triphenylphosphane in 15 ml of dry tetrahydrofuran, 0.7 ml of diethyl azodicarboxylate (DEAD) are added dropwise. The mixture is stirred overnight at room temperature, the solvent evaporated off and the residue purified by chromatography. The title compound is obtained (m.p. 247–251°).

B) 2-tert-Butyl-benzoxazol-6-ol (formula II)

A mixture of 1.01 ml of pivaloyl chloride, 808 mg 2,4-dihydroxyaniline hydrochloride (formula V) and 0.4 ml of pyridine is heated at about 210° for about 18 hours. The mixture obtained is dispersed in a mixture of cyclohexane and ethyl acetate and purified by chromatography. The title compound is obtained (m.p. 204–210°).

C) 2-(Adamantan-2-ylidenemethyl)benzoxazol-6-ol (formula IIa) and 2-(2-hydroxyadamantan-2-ylmethyl)benzoxazol-6-ol (formula IIc)

To a solution of 6.6 g 2-methyl-benzoxazol-6-ol (formula IIb) in 100 ml of dry tetrahydrofuran, cooled to 0°, N-ethyldiisopropylamine and trimethylsilyl chloride are added. The mixture is stirred at room temperature for about 2 hours, cooled to −78°, and sodium bis(trimethylsilyl)amide solution is added in portions. To the mixture obtained solid 2-adamantanone (formula VI) is added and the mixture is kept at −78° for about one hour. The reaction mixture is allowed to warm up to room temperature and is pointed into 300 ml of 1 M NaHSO4 solution. The mixture is extracted with ethyl acetate and the organic layer is dried over sodium sulfate. The solvent is evaporated off and the residue is purified by chromatography. The above title compounds are obtained (m.p., respectively, 248–253° and 238–240°).

Alternatively, in order to maximize the yield of the first title compound above, the evaporation residue obtained is treated with 240 ml of toluene, 3.1 ml of trifluoroacetic acid are added, and the reaction mixture is heated at about 115° for about 7 hours and cooled. Crystallization occurs. The first title compound above is obtained in the form of a crystalline salt with trifluoroacetic acid. This is recrsytallized in ethanol. The compound in free form is obtained (m.p. 248–253°).

D) 2-(Adamantan-2-ylidenemethyl)benzothiazol-5-ol (formula IIa)

300 mg 2-(5-methoxy-benzothiazol-2-ylmethyl) adamantan-2-ol (formula IX) and 527 mg pyridine hydrochloride are heated at about 200° for about 30 minutes. The melt obtained is dissolved in 100 ml of ethyl acetate, the mixture is extracted with water, 2.5 M sodium acetate solution and brine, the organic phase dried and the solvent evaporated off. The evaporation residue obtained is subjected to chromatography. The title compound is obtained (m.p. 156–158°).

E) 2-(Cycloheptylidenemethyl)benzothiazol-5-ol (formula IIa)

By reacting 120 mg 2-(cycloheptylidenemethyl)-5-methoxybenzothiazole (formula X) as described under D) above, the title compound is obtained (m.p. 105–120°).

Analogously as described under A) to E) above and using appropriate starting materials, the following compounds of formula II are obtained:

2-(2,2-Dimethylpropyl)benzoxazol-6-ol (m.p. 176–184°);

2-(Adamantan-1-yl)benzoxazol-6-ol (m.p. 260–265°);

2-Tridecyl-benzoxazol-6-ol (m.p. 72–73°);

2-(2,2-Diphenylethyl)benzoxazol-6-ol (m.p. 182–206°);

2-(2,2,2-Triphenylethyl)benzoxazol-6-ol (m.p. 150–155°);

2-Dicyclohexylmethyl-benzoxazol-6-ol (m.p. 196–204°);

[1-(6-Hydroxy-benzoxazol-2-yl)-2,2-dimethylpropyl] carbamic acid tert-butyl ester (m.p. 131–160°);

2-(Hexahydro-2,5-methano-pentalen-3a-yl)benzoxazol-6-ol (m.p. 241–243°);

2-(7-Isopropyl-1,4a-dimethyl-1,2,3,4,4a,5,6,10,10a-decahydrophenanthren-1-yl)benzoxazol-6-ol (m.p. 90–95°);

2-(Cyclohexylidenemethyl)benzoxazol-6-ol (m.p. 158–162°);

2-(Cyclobutylidenemethyl)benzoxazol-6-ol (m.p. 200–203°);

2-(Cyclopentylidenemethyl)benzoxazol-6-ol (m.p. 168–172°);

2-(Cycloheptylidenemethyl)benzoxazol-6-ol (m.p. 141–142°);

2-(Cyclododecanylidenemethyl)benzoxaol-6-ol (m.p. 155–157°);

2-(Bicyclo[3.3.1]non-9-ylidenemethylbenzoxazol-6-ol (m.p. 221–223°);

2-(9-Hydroxy-bicyclo[3.3.1]non-9-ylmethyl)benzoxazol-6-ol (m.p. 221–223°);

2-(2,2-Dimethyl-cyclohexylidenemethyl)benzoxazol-6-ol ($^{13}$C13-NMR [CDCl$_3$/CD$_3$OD]: 163.552, 162.497, 154.865, 150.599, 134.691, 119.197, 112.951, 106.621, 97.295, 41.928, 38.100, 27.979, 27.915, 26.931, 22.141);

2-(2-Methoxy-cyclohex-(Z)-ylidenemethyl)benzoxazol-6-ol (m.p. 157–160°);

2-(2-Methoxy-cyclohex-(E)-ylidenemethyl)benzoxazol-6-ol (m.p. 148–150°);

2-(4-Ethylcyclohexylidenemethyl)benzoxazol-6-ol (m.p. 137–139°);

2-(3,3,5,5-Tetramethylcyclohexylidenemethyl) benzoxazol-6-ol (m.p. 161–163°);

2-(1,4-Dioxa-spiro[4.5]dec-8-ylidenemethyl)benzoxazol-6-ol (m.p. 154–156°);

2-(3,3-Dimethyl)-1,5-dioxa-spiro[5,5]undec-9-ylidenemethyl)benzoxazol-6-ol (m.p. 194–196°);

2-[Octahydronaphthal-1-ylidenemethyl)benzoxazol-6-ol (m.p. 160–162°);

2-(2-Butylhex-1-ylidene)benzoxazol-6-ol (m.p. 76–80°);

2-(2-Pentylhept-1-ylidene)benzoxazol-6-ol: ($^{13}$C-NMR [CDCl$_3$/CD$_3$OD]: 162.626, 158.774, 156.116, 151,451, 134.282, 119.369, 113.678, 111.164, 97.619, 39.046, 32.974, 32.458, 32.018, 28.723, 28.150, 22.974, 22.857, 14.188);

2-(2-Hexyloct-1-ylidene)benzoxazol-6-ol ($^{13}$C-NMR [CDCl$_3$/CD$_3$OD: 125.8 MHz]: 162.307, 158.269, 154.347, 150.785, 135.067, 119.352, 113.021, 110.771, 97.518, 38.504, 32.597, 31.645, 31.576, 29.409, 28.981, 28.410, 27.883, 22.511, 13.979);

2-(2-Heptylnon-1,2-ylidene)benzoxazol-6-ol ($^{13}$C-NMR [CDCl$_3$/CD$_3$OD]: 162.640, 158.877, 156.143, 151.466, 134.266, 119.355, 113.694, 111.165, 97.638, 39.091, 33.033, 32.283, 30.194, 29.800, 29.643, 29.563, 29.075, 28.495, 23.106, 14.256);

2-(1-Hydroxyadamantan-2-yl)ethyl]benzoxazol-6-ol; ($^{13}$C-NMR [CDCl$_3$/CD$_3$OD]: 119.169, 112.873, 97.4021, 38.110, 37.333, 36.660, 34.264, 33.568, 33.126, 32.878, 32.681, 26.978, 12.195);

2-(1-Adamantan-2-ylidene-ethyl)benzoxazol-6-ol (oil);

2-[1-(2-Hydroxyadamantan-2-yl)pentyl]benzoxazol-6-ol ($^{13}$C-NMR: 119.037, 113.029, 97.790, 31.204, 28.435, 26.423, 22.184, 13.797);

2-(1-Adamantan-2-ylidene-pentyl)benzoxazol-6-ol (oil);

2-(5,6,7,8-Tetrahydronaphthalin-1-yl)benzoxazol-6-ol (m.p. 120–122°);

2-(Cyclobutylidenemethyl)benzoxazol-5-ol (m.p. 169–170°);

2-(Bicyclobutylidene-(2E)-ylidenemethyl)benzoxazol-5-ol (oil);

2-(Cyclopentylidenemethyl)benzoxazol-5-ol (m.p. 174–175°);

2-(Cyclohexylidenemethyl)benzoxazol-5-ol (m.p. 144–145° C.);

2-(Cyclohex-1-enylmethyl)benzoxazol-5-ol (oil);

2-(Cycloheptylideenmethyl)benzoxazol-5-ol (m.p. 93–95°);

2-(Cyclododecanylidenemethyl)benzoxazol-5-ol (m.p. 170–172°);

2-(Bicyclo[3.3.1]non-9-ylidenemethyl)benzoxazol-5-ol (m.p. 177–178°);

2-(9-Hydroxy-bicyclo[3.3.1]non-9-ylmethyl)benzoxazol-5-ol (m.p. 218–219°);

2-(1-Hydroxy-2,2-dimethylcyclohexylmethyl)methyl) benzoxazol-5-ol (m.p. 166–168°);

2-(2,2-Dimethylcyclohexylidenemethyl)benzoxazol-5-ol (oil);

2-(2-Methoxycyclohex-(Z)-ylidenemethyl)benzoxazol-5-ol ($^{13}$C-NMR; 125.8 MHz; 162.709, 155.743, 153.888, 144.335, 142.170, 113.849, 112.059, 110.422, 105.244, 73.709, 55.602, 33.297, 32.882, 28.577, 20.122);

2-(2-Methoxycyclohex-(E)-ylidenemethyl)benzoxazol-5-ol (m.p. 141–144°);

2-(4-Ethylcyclohexylidenemethyl)benzoxazol-5-ol ($^{13}$C-NMR [CDCl$_3$/CD$_3$OD]): 165.203, 160.259, 155.998, 145.294, 142.867, 114.835, 111.739, 109.631, 105.497, 40.269, 38.948, 35.672, 34.921, 31.423, 30.305, 12.672);

2-(3,3,5,5-Tetramethylcyclohexylidenemethyl) benzoxazol-5-ol (m.p. 138–139°);

2-(1,4-Dioxa-spiro[4.5]dec-8-ylidenemethyl)benzoxazol-5-ol ) (m.p. 160–162°);

2-(3,3-Dimethyl-1,5-dioxa-spiro[5.5]undec-9-ylidenemethyl)benzoxazol-5-ol; (m.p. 137–140°);

2-(Adamantan-2-ylidenmethyl)benzoxazol-5-ol (m.p. 160–162°);

2-[1-(2-Hydroxyadamantan-2-yl)ethyl]benzoxazol-5-ol (m.p. 125–130°);

2-(1-Adamantan-2-ylidene-ethyl)benzoxazol-5-ol (oil); and 2-(Adamantan-2-ylidenmethyl)benzthiazol-6-ol (m.p. 289–293°).

F) 2-(Adamantan-1-yl)-N-(2,4-dihydroxy-phenyl)acetamide (formula VII)

1.05 ml of N-ethyl-diisopropylamine is added to a solution of 323 mg 2,4-dihydroxyaniline hydrochloride (formula V), 388 mg (adamantan-1-yl)acetic acid (formula R$_3$COOH) and 1.2 ml of propylphosphonic anhydride (50% in ethyl acetate) in 20 ml of dry dichloromethane at 0°. The mixture obtained is stirred for about 18 hours at room temperature and the solvent is evaporated off. The residue is dissolved in 50 ml of ethyl acetate and extracted with 1 M aqueous hydrochloric acid, saturated aqueous NaHCO$_3$ solution and brine. The organic layer is dried and the solvent is evaporated off. The title compound is obtained (m.p. 195–197°).

G) 2-(Adamantan-2-ylidene)-N-(2,4-dihydroxyphenyl) acetamide (formula VII) 3.0 g (adamantan-2-ylidene)acetic acid (formula R$_3$COOH), 5.91 g triphenylphosphane and 4.95 g dipyridyldisulfide, dissolved in 100 ml of dichloromethane, are stirred at room temperature overnight. To the mixture obtained, 5.13 ml of N-ethyl-diisopropylamine and 4.83 g 2,4-dihydroxyaniline hydroxide (formula V) are added and the mixture is stirred for about 24 hours, the solvent is evaporated off, the evaporation residue is dissolved in ethyl acetate and extracted with a saturated aqueous NaH$_2$PO$_4$ solution and brine. The organic layer is dried, the solvent is evaporated off and the residue is purified by chromatography. The title compound is obtained (m.p. 166–169°).

The following compounds of formula VII are obtained in analogous manner as described under F) and G) above:

N-(2,4-Dihydroxyphenyl)-3,3-dimethyl-butyramide: [$^1$H-NMR (CDCl$_3$): 7.41 (s, 1H), 6.78 (d, J=8.5 Hz, 1H), 6.49 (d, J=2.7 Hz, 1H), 6.34 (dd, J=2.7+8.5 Hz, 1H), 2.29 (s, 2H), 1.10 (s, 9H)];

Adamantane-1-carboxylic acid (2,4-dihydroxyphenyl) amide (m.p. 108–110°);

Tetradecanoic acid (2,4-dihydroxyphenyl)amide (m.p. 110–112°);

N-(2,4-Dihydroxyphenyl)-3,3-diphenyl-propionamide (m.p. 206–208°);

N-(2,4-Dihydroxyphenyl)-3,3,3-triphenyl-propionamide (m.p. 234–235°);

2,2-Dicyclohexyl-N-(2,4-dihydroxyphenyl)acetamide (m.p. 179–181°);

[1-(2,4-Dihydroxy-phenylcarbamoyl)-2,2-dimethylpropyl]carbamic acid tert.-butyl ester (m.p. 88–91°);

Hexahydro-2,5-methano-pentalene-3a-carboxylic acid (2,4-dihydroxyphenyl)amide (m.p. 204–206°);

7-Isopropyl-1,4a-dimethyl-1,2,3,4,4a,4b,5,6,10,10a-decahydrophenanthren-1-carboxylic acid (2,4-dihydroxyphenyl)amide (m.p. 200–207°);

2-Cyclohexylidene-N-(2,4-dihydroxyphenyl)acetamide [$^1$H-NMR (CDCl$_3$): 6.85 (d, J=8.6 Hz, 1H), 6.42 (d, J=2.7 Hz, 1H), 6.27 (dd, J=2.7+8.6 Hz, 1H), 5.69 (s, 1H), 2.82 (bm, 2H), 2.16 (bm, 2H), 1.60 (s, 6H)]; and 5,6,7,8-Tetrahydronaphthalene-1-carboxylic acid (2,4-dihydroxyphenyl)-amide (m.p. 168–174°).

H) 2-(Cycloheptan-2-ylidenemethyl)-5-methoxy-benzothiazole (formula X)

187 µl of methanesulfonyl chloride are added to a mixture of 350 mg of 2-(5-methoxybenzothiazol-2-ylmethyl) cycloheptan-2-ol (formula IX), 665 µl of triethylamine and a catalytical amount of 4-N,N-dimethylaminopyridine in 12 ml of dry dichloromethane at about 0°. The mixture is stirred for about 12 hours at room temperature, 187 µl of methansulfonyl chloride and 665 µl of triethylamine are added and the resultant reaction mixture is stirred at about 40° for about 48 hours. The mixture is diluted with 100 ml of ethyl acetate and then extracted with 1 M aqueous hydrochloric acid, saturated aqueous sodium bicarbonate solution and brine. The organic phase is dried and the solvent is evaporated off. The residue is subjected to chromatography. The title compound is obtained [$^{13}$C-NMR (125.8 MHz): 166.528, 158.978, 155.645, 154.597, 126.878, 121.337, 119.750, 114.743, 105.127, 55.561, 39.394, 33.143, 29.921, 29.344, 28.775, 26.435], I) 2-(5-Methoxybenzothiazol-2-ylmethyl)adamantan-2-ol (formula IX)

2.5 mL of a 1.6 M n-butyllithium solution is hexane are added dropwise to a solution of 358 mg of 5-methoxy-2-methylbenzothiazole (formula VIII) in 5 ml of dry THF, cooled to about −78° and the mixture obtained is stirred for about one hour. Solid 2-adamantanone (formula VI) is added and the mixture is kept at −78° for about one hour. The mixture is allowed to warm to room temperature and 400 µl of acetic acid are added. The resultant mixture is diluted with 600 ml of ethyl acetate and extracted with saturated NaH$_2$PO$_4$ solution. The solvent of the organic phase is evaporated off and the residue obtained is subjected to chromatography. The title compound is obtained (m.p. 140–142°).

The following compounds of formula IX are obtained in analogous manner as described under I) above.

2-(5-Methoxy-benzothiazol-2-ylmethyl)cycloheptan-2-ol
[$^{13}$C-NMR (125.8 MHz): 169.841, 159.007, 154.324, 121.540, 115.095, 105.275, 75.529, 55.605, 46.163, 41.063, 29.665, 22.300]; and 2-(6-Methoxy-benzothiazol-2-ylmethyl)adamantan-2-ol (m.p. 161–163°).

The compounds of the invention, in particular the compounds of formula I, in free form or pharmaceutically acceptable salt form, including as solvates, hereinafter briefly named "the agents of the invention", possess pharmacological activity. They are indicated for use as pharmaceuticals. In particular, they inhibit steroid sulfatase activity.

Steroidal hormones in particular tissues are associated with several diseases, such as tumors of the breast, endometrium and prostate. Important precursors for the local production of these steroid hormones are steroid 3-O-sulfates which are desulfated by the enzyme steroid sulfatase in the target tissues. In addition of this enzyme results in therapeutically relevant, reduced local levels of the corresponding active steroidal hormones. Furthermore, steroid sulfatase inhibitors may also be immunosuppressive, and enhance memory when delivered to the brain.

The agents of the invention reduce endogenous levels of the androgens and/or estrogens in skin and are thus particularly indicated for use in the prevention or treatment of androgen-dependent disorders of the pilosebaceous unit, such as acne, seborrhea, androgenic alopecia and hirsutism, and in the topical treatment of squamous cell carcinoma.

The agents of the invention are therefore indicated for use as steroid sulfatase inhibitors, particularly in the prevention and treatment of illnesses responsive to steroid sulfatase inhibition, such as illnesses in which the steroid products of sulfatase cleavage play a role, in particular in the prevention and treatment of the following specific conditions: androgen-dependent disorders of the pilosebaceous unit such as acne, seborrhea, androgenic alopecia and hirsutism; cancer, especially estrogen- and androgen-dependent tumors such as tumors of the breast, endometrium and prostate, and squamous cell carcinoma; inflammatory and autoimmune diseases such as rheumatoid arthritis, type I and II diabetes, systemic lupus erythematosus, multiple sclerosis, myastenia gravis, thyroiditis, vasculitis, ulcerative colitis and Chrohn's disease; skin disorders such as psoriasis, eczema and contact dermatitis; graft versus host disease; asthma; organ rejection following transplantation; and for enhancement of cognitive function, as in senile dementia, including Alzheimer's disease, by increasing DHEAS (dehydroepiandrosteron) levels in the central nervous system.

The above activities can be shown e.g. in the following assays:

1. Steroid sulfatase inhibition in vitro:

Human steroid sulfatase is obtained in pure form as described in WO 99/52890 and the assay is effected as follows:

Purified human steroid sulfatase not only is capable of cleaving steroid sulfates, but also readily cleaves aryl sulfates, such as p-nitrocatechol sulfate which is used herein. Assay mixtures are prepared by consecutively dispensing the following solutions into the wells of flat-bottom microtiter plates:

1) 50 μl inhibitor dilution in buffer (=0.1 M Tris-HCl, ph 7.5, 0.1% Triton X-100);
2) 50 μl substrate (=20 mM p-nitrocatechol sulfate in buffer)
3) 50 μl enzyme dilution to give a final concentration of 75 nM steroid sulfatase.

Plates are incubated at 37° C. for 30 minutes. The assay is stopped by addition of 100 μl of 1 N NaOH, and optical density measured in a microplate reader at 492 nm. Compounds are added from stock solutions in ethanol; the final ethanol concentration does not exceed 0.1%. $IC_{50}$ values are calculated by nonlinear regression of the concentration/optical density data using the program Grafit (Erithacus Ltd.). Reported values are the result of three determinations.

From the fluorescence intensity data (I) obtained at different concentrations (c) of the test compound, the concentration inhibiting the enzymatic activity at 50% ($IC_{50}$) is calculated using the equation $$I = \frac{I_{100}}{1 + (c/IC_{50})^s}$$

wherein $I_{100}$ is the intensity observed in the absence of inhibitor and s is the slope factor.

Estrone-3-O-sulfamate serves as reference compound and its $IC_{50}$ value is determined in parallel to the test compounds and is about 60 mM. Relative $IC_{50}$ values (rel $IC_{50}$) are defined as follows:

$$rel\, IC_{50} = \frac{IC_{50} \text{ of test compound}}{IC_{50} \text{ of estrone sulfamate}}$$

The agents of the invention inhibit steroid sulfatase in this assay with real $IC_{50}$ values in the range of about 0.1 to 30.

2. Steroid sulfatase inhibition in the CHO/STS assay:

CHO cells stably transfected with human steroid sulfatase (CHO/STS) are seeded into microtiter plates. After reaching approximately 90% confluency, they are incubated overnight with graded concentrations of test substances. They are then fixed with 4% paraformaldehyde for 10 minutes at room temperature and washed 4 times with PBS before incubation with 100 μl/well 0.5 mM 4-methylumbelliferyl sulfate (MUS) dissolved in 0.1M Tris-HCl, pH 7.5. The enzyme reaction is carried out at 37° C. for one hour. Then 50 μl/well stop solution (1M Tris-HCl, pH 10.4) are added. The enzyme reaction solutions are transferred to white plates (Microfluor, Dynex, Chantilly, Va., USA) and read in a Fluoroskan II fluroescence microtiter plate reader. Reagent blanks are subtracted from all values. For drug testing, the fluorescence units (FU) are divided by the optical density readings after staining cellular protein with sulforhodamine B ($OD_{550}$) in order to correct for variations in cell number. $IC_{50}$ values are determined by linear interpolation between two bracketing points. In each assay with inhibitors, estrone 3-O-sulfamate is run as a reference compound, and the $IC_{50}$ values are normalized to estrone 3-O-sulfamate:

relative $IC_{50}$=$IC_{50}$ compound/$IC_{50}$ estrone 3-O-sulfamate.

In this assay the agents of the invention inhibit steroid sulfatase with real $IC_{50}$ values in the range 0.8–165, corresponding to absolute $IC_{50}$ values in the range 32 nM to 7800 nM.

For the above use in steroid sulfatase inhibition the dosage to be used will vary, of course, depending e.g. on the particular agent employed, the mode of administration and the treatment desired. However, in general, satisfactory results are obtained when the agents are administered at a daily dose of from about 0.1 mg/kg to about 100 mg/kg animal body weight, conveniently given in divided doses two to four times daily. For most large mammals the total daily dosage is from about 5 mg to about 5000 mg, conveniently administered, for example, in divided doses up to four times a day or in retarded form. Unit dosage forms comprise, e.g. from about 1.25 mg to about 2000 mg of the agents in admixture with at least one solid or liquid pharmaceutically acceptable carrier or diluent.

The agents of the invention may be administered in similar manner to known standards for use in such indications. The agents of the invention may be admixed with conventional, chemotherapeutically acceptable carriers and diluents and optionally further excipients, and administered e.g. orally e.g. in the form of formulations, e.g. in the form of tablets and capsules.

Alternatively, the agents may be administered topically, e.g. in the form of formulations, e.g. lotions, solutions, ointments or creams; or parenterally or intravenously. The concentration of active substance will of course vary, e.g. depending on the agent employed, the treatment desired and the nature of the form or formulation used. In general, satisfactory results are obtained in e.g. topical formulations at concentrations of from about 0.5% to about 5%, particularly from about 0.1% to about 1% by weight.

The invention therefore also provides:

an agent of the invention for use as a pharmaceutical, especially as a steroid sulfatase inhibitor;

a pharmaceutical composition comprising an agent of the invention together with at least one pharmaceutically acceptable carrier or diluent;

a process for the preparation of a pharmaceutical composition having an agent of the invention together with at least one pharmaceutically acceptable carrier or diluent, comprising mixing an agent of the invention together with at least one pharmaceutically acceptable carrier or diluent;

a method of prevention or treatment of illnesses responsive to steroid sulfatase inhibition comprising administering a therapeutically effective amount of an agent of the invention to a subject in need of such treatment; and the use of an agent of the invention in the preparation of a medicament for prevention or treatment of illnesses responsive to steroid sulfatase inhibition.

The invention includes the agents of the invention for use in particular in the prevention or treatment of an hydrogen-dependent disorders of the pilosebaceous unit, such as acne, seborrhea, androgenic alopecia and hirsutism, and in the topical treatment of squamous cell carcinoma, as well as for use in enhancement of cognitive function.

The agents of the invention are particularly beneficial as regards side effect profile and chemical stability and thus well-suited for e.g. long term storage of topical galenical forms.

The compound of Example 12, namely sulfamic acid 2-(adamantan-2-ylidenemethyl)benzoxazol-6-yl ester, is the most preferred agent of the invention in the above indications. It has, for example, been determined that in the above assay 1., this agent has a rel $IC_{50}$ value of 4.6 and an absolute $IC_{50}$ value of about 0.97 $\mu$M, and in the above assay 2., a rel $IC_{50}$ value of 1.25.

What is claimed is:

1. A benzoxa- or benthiazole substituted at the 2 position and carrying a sulfamic acid ester group bound via oxygen to the phenol part of the ring structure.

2. A compound according to claim 1 of formula $Ip_1$

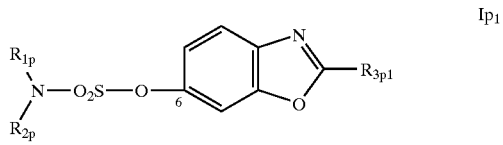

wherein either $R_{1p}$ and $R_{2p}$ have the significances indicated in claim 1 for $R_1$ and $R_2$; and $R_{3p1}$ is alkyl; alkenyl; alkinyl; cycloalkyl; acyl; cycloalkylalkyl; arylalkyl; arylalkenyl; arylalkinyl; heteroaryl; or heteroarylalkyl; or $R_{1p}$ and $R_{2p}$ are hydrogen; and $R_{3p1}$ is adamantan-2-ylidenemethyl; or of formula $Ip_2$

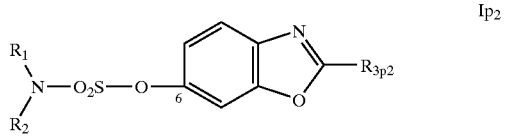

wherein $R_1$ and $R_2$ are as defined in claim 1; and $R_{3p2}$ is alkyl; alkenyl; alkinyl; cycloalkyl; acyl; cycloalkylalkyl; adamantylalkenyl, including adamantanylidenalkyl; arylalkyl; arylalkyl; arylalkenyl; arylalkinyl; heteroaryl; or heteroarylalkyl;

in free form or salt form.

3. A compound according to claim 1 or 2 of formula $Ip_1$

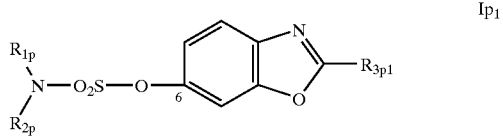

wherein either $R_{1p}$ and $R_{2p}$ have the significances indicated in claim 2 for $R_1$ and $R_2$; and $R_{3p1}$ is alkyl; alkenyl; alkinyl; cycloalkyl; acyl; cycloalkylalkyl; arylalkyl; arylalkenyl; arylalkinyl; heteroaryl; or heteroarylalkyl; or $R_{1p}$ and $R_{2p}$ are hydrogen; and $R_{3p1}$ is adamantan-2-ylidenemethyl; or of formula $Ip_2$

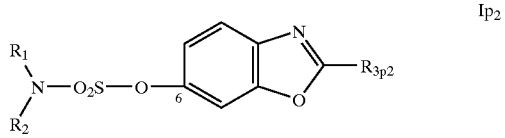

wherein $R_1$ and $R_2$ are as defined in claim 2; and $R_{3p2}$ is alkyl; alkenyl; aylkinyl; cycloalkyl; acyl; cycloalkylalkyl; adamantylalkenyl, including adamantanylidenalkyl; arylalkyl; arylalkenyl; arylalkinyl; heteroaryl; or heteroarylalkyl;

in free form or salt form.

4. Sulfamic acid 2-(adamantan-2-ylidenemethyl)benzoxazol-6-yl ester in free form or salt form.

5. A compound according to claim 1 or 2 in free form of pharmaceutically acceptable salt form for use as a pharmaceutical.

6. A pharmaceutical composition comprising a compound according to claim 1 or 2 in free form or pharmaceutically acceptable salt form together with at least one pharmaceutically acceptable carrier or diluent.

7. A process for the preparation of a pharmaceutical composition comprising mixing a compound according to claim 1 or 2 in free form or pharmaceutically acceptable salt form together with at least one pharmaceutically acceptable carrier or diluent.

8. A method of prevention or treatment of illnesses responsive to steroid sulfatase inhibition comprising administering a therapeutically effective amount of a compound according to claim 1 or 2 in free form or pharmaceutically acceptable salt form to a patient in need of such treatment.

9. A process for the preparation of a compound according to claim 1 or 2, comprising sulfamoylating a corresponding benzoxa- or benzthiazole substituted in the 2 position and carrying a hydroxyl group on the phenyl part of the ring structure, specifically, for the preparation of a compound of formula I as defined in claim 2, in free form or salt form, comprising a) when $R_1$ and $R_2$ are both hydrogen, sulfamoylating a compound of formula II

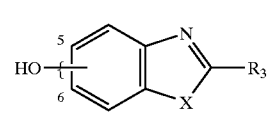

II wherein X and $R_3$ are as defined in claim 2, or b) when one or both of $R_1$ and $R_2$ are other than hydrogen, appropriately N-substituting a compound of formula I wherein $R_1$ and $R_2$ are both hydrogen, and recovering the resultant compound in free form or salt form.

\* \* \* \* \*

UNITED STATES PATENT AND TRADEMARK OFFICE
CERTIFICATE OF CORRECTION

PATENT NO. : 6,716,865 B1
DATED : April 6, 2004
INVENTOR(S) : Billich et al.

It is certified that error appears in the above-identified patent and that said Letters Patent is hereby corrected as shown below:

Title page,
Item [*] Notice, delete "0 days" and insert -- (56 days) --.

Signed and Sealed this

Fourth Day of January, 2005

JON W. DUDAS
*Director of the United States Patent and Trademark Office*